United States Patent [19]

Kanojia

[11] 4,360,467

[45] Nov. 23, 1982

[54] PROCESS FOR PREPARING 8-OXABICYCLO[3.2.1]-OCTANE-1-ACETIC ACIDS

[75] Inventor: Ramesh M. Kanojia, Somerville, N.J.

[73] Assignee: Ortho Pharmaceutical Corporation, Raritan, N.J.

[21] Appl. No.: 299,704

[22] Filed: Sep. 8, 1981

Related U.S. Application Data

[62] Division of Ser. No. 237,321, Feb. 23, 1981, Pat. No. 4,322,357.

[51] Int. Cl.$^3$ .............................................. C07D 309/06
[52] U.S. Cl. .................................. 549/397; 556/415; 556/416; 556/417; 556/482; 568/347
[58] Field of Search ................. 260/345.7 R, 345.8 R, 260/345.9 R, 340.9 R; 556/416

[56] References Cited

U.S. PATENT DOCUMENTS

| | | | |
|---|---|---|---|
| 4,102,895 | 7/1978 | Kanojia | 260/345.9 R |
| 4,182,717 | 1/1980 | Chen | 260/345.8 R |
| 4,237,053 | 12/1980 | Kane | 260/345.9 R |
| 4,237,054 | 12/1980 | Chen | 260/345.7 R |

*Primary Examiner*—Nicky Chan
*Attorney, Agent, or Firm*—Benjamin F. Lambert

[57] ABSTRACT

The preparation of racemic 1R, 4R, 5R-5-(4', 8'-dimethyl-5'-hydroxy-7'-nonenyl)-5-methyl-8-oxabicyclo[3.2.1]-octane-1-acetic acid is described. The cycloheptane compounds are active uteroevacuant agents.

7 Claims, No Drawings

PROCESS FOR PREPARING 8-OXABICYCLO[3.2.1]-OCTANE-1-ACETIC ACIDS

This is a division, of application Ser. No. 237,321, filed Feb. 23, 1981, now U.S. Pat. No. 4,322,357.

The present invention relates to novel cycloheptane compounds having the following formula.

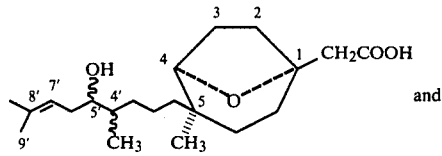

I-A and

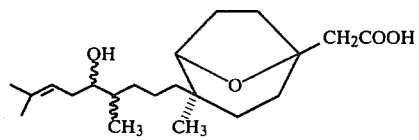

I-B

In compound IA the 4-oxygen and the 5-methyl group are cis while in compound IB the 4-oxygen and the 5-methyl group are trans.

The novel cycloheptane compounds are prepared as racemic mixtures according to the scheme outlined below. Although four diasterioisomers are formed with respect to the ring chiral centers at $C_1$, $C_4$ and $C_5$ during the course of the reactions, for the purpose of simplification only the 1R, 4R, 5R (I-A) and 1S, 4S, 5R (I-B) structures are shown. The stereochemistry of the side chain chiral centers at $C_5'$ and $C_6'$ is unspecified to indicate that all the possible isomers with respect to these centers are also formed. In total, sixteen isomers are formed, as theoretically expected with respect to all the chiral centers ($C_1$, $C_4$, $C_5$, $C_5'$ and $C_6'$, the stereochemistry at $C_1$ being dictated by that at $C_4$).

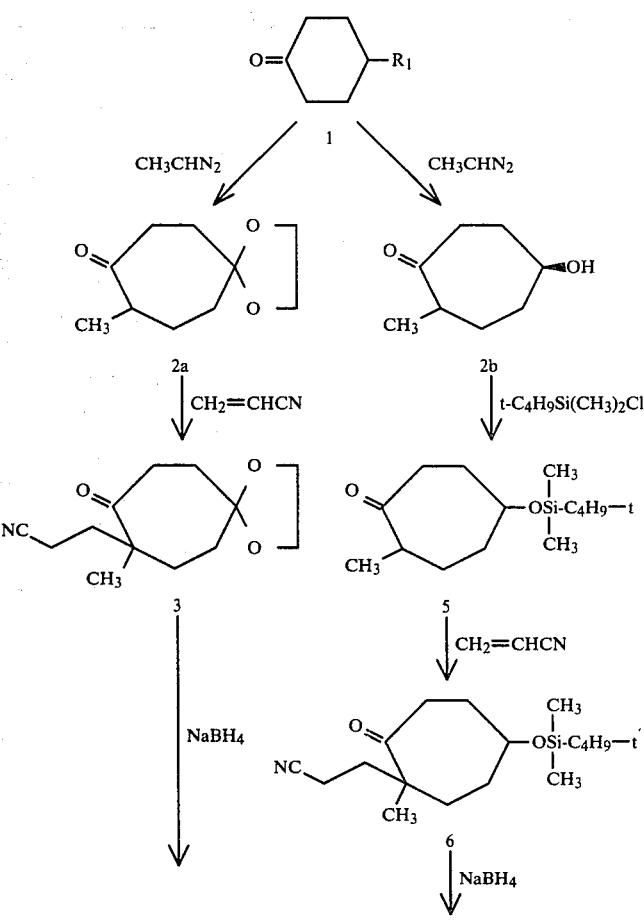

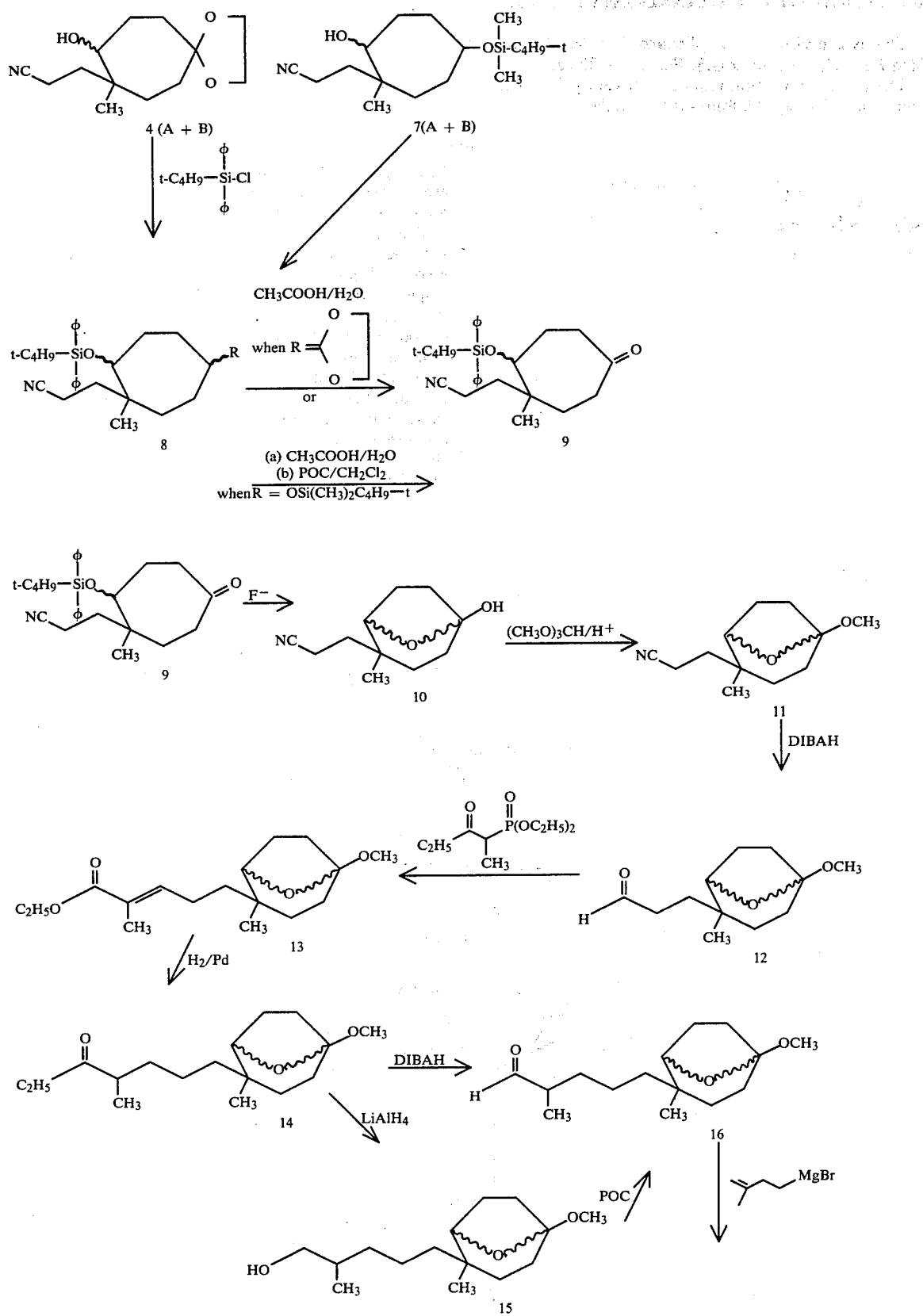

-continued
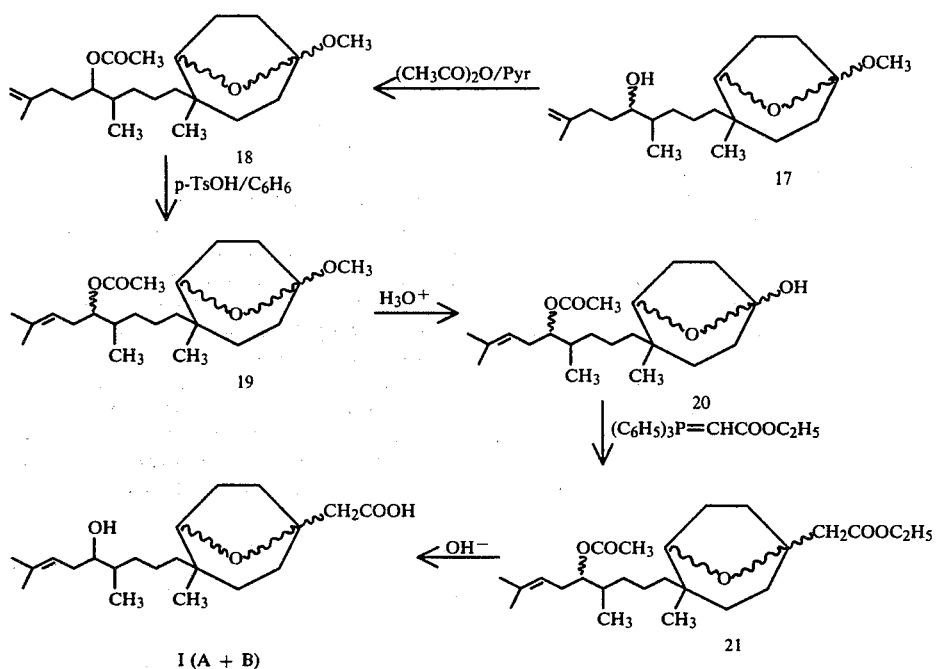
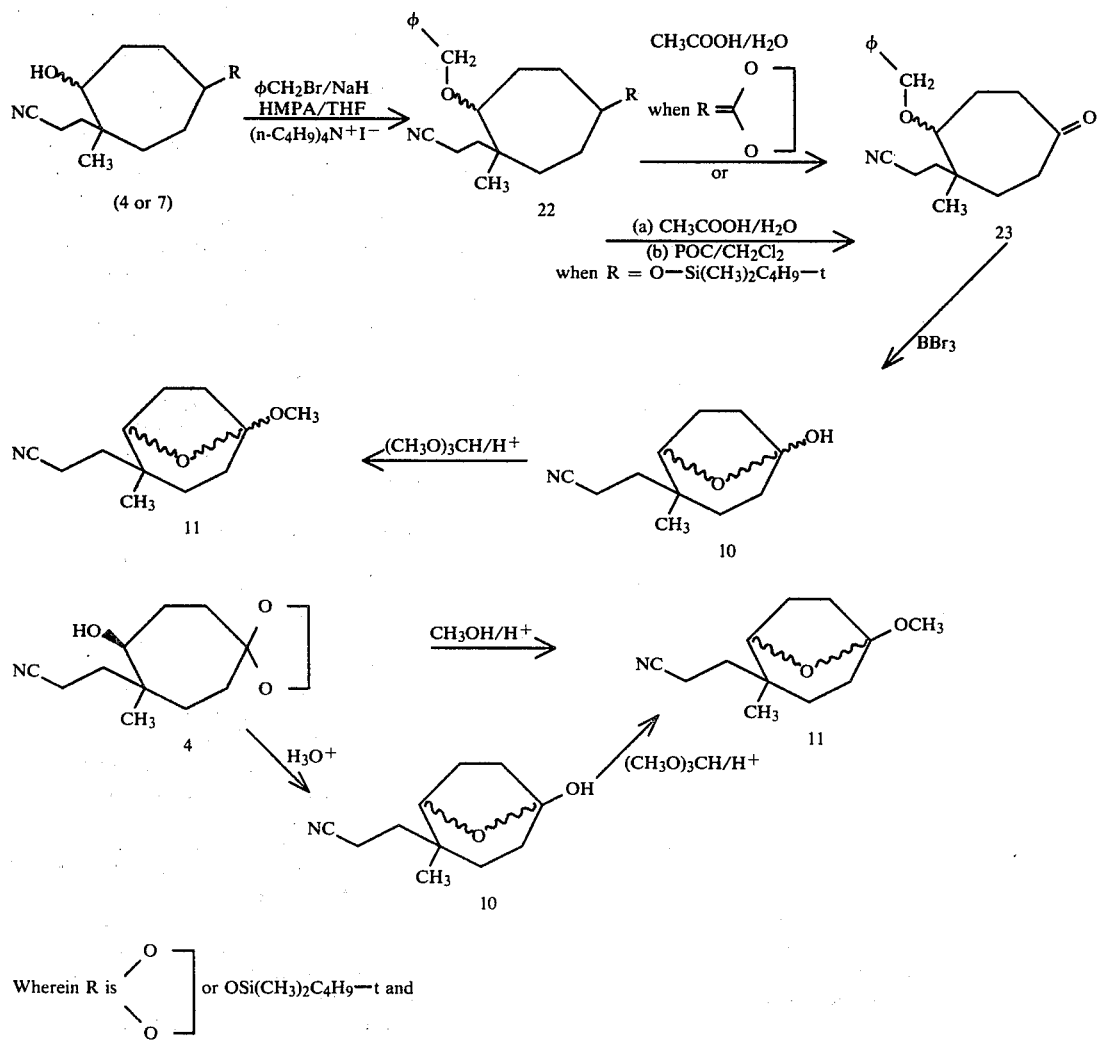

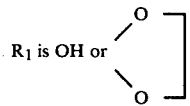

In the above schemes, PCC is pyridinium chlorochromate; DIBAH is diisobutylaluminum hydride; TsOH is tosic acid; THF is tetrahydrofuran; and HMPA is hexamethylphosphoramide.

The first step in the preparation of the cycloheptane compounds (IA and IB) involves the reaction of a cyclohexanone (1) with diazoethane to form the appropriate 5-oxygen-substituted-2-methylcycloheptanone 2a or 2b. The reaction is carried out in a suitable solvent such as ethanol or ether, and at a temperature between −10° C. and room temperature. The hydroxy group of the 5-hydroxy compound (2b) is protected by converting it to the t-butyldimethylsilyl ether (5) by reaction with the corresponding silyl chloride in a suitable solvent such as dimethylformamide. The appropriately 5-protected cycloheptanone (2a or 5) is then alkylated by means of a base catalyzed Michael addition with acrylonitrile to afford the corresponding 2-cyanoethylated-2-methylcycloheptanone (3 or 6). The reaction is carried out in a suitable solvent such as dimethoxyethane, for example, at a temperature between about −15° C. and room temperature. Reduction of the keto group with a suitable reducing agent, such as sodium borohydride or potassium borohydride, for example, in a suitable solvent such as ethyl alcohol, methanol, water, tetrahydrofuran, and the like, gives an approximately 30:70 mixture of the corresponding epimeric cycloheptanols of 4 or of 7 wherein the hydroxyl group and the methyl group are both cis (A) and wherein the hydroxyl group and the methyl group are both trans (B). The epimeric cycloheptanols can be separated by physical means such as, for example, chromatography on silica gel using mixtures of ethyl acetate and hexane as the eluent or by preparative liquid chromatography. The isolation of the stereochemically pure epimers of cycloheptanols (4 and 7) at this stage establishes the basis for sequentially obtaining the various intermediates and the end product acids (IA and IB) as a single pair of stereoisomers (IA or IB).

When either of the purified epimers (4A or 4B or 7A or 7B) is employed as the starting material for the synthesis of the 8-oxabicyclo[3.2.1]octane-1-acetic acid, stereoselective synthesis of the corresponding isomers (IA and IB) is effected. For convenience, the synthetic sequences are illustrated using a mixture of the 4(A&B) or 7(A&B) isomers. The individual isomers for each of the intermediate compounds in the sequence are easily determined in mixtures by virtue of the relatively constant NMR characteristics of the respective angular methyl groups.

The free hydroxyl group in the cycloheptanol (4 or 7) is then protected by converting the cycloheptanol to the acid resistant t-butyldiphenylsilyl ether derivative (8). The acid labile t-butyldimethylsilyl group is selectively removed with aqueous acid to give a cycloheptanol which upon oxidation with pyridinium chlorochromate affords the corresponding ketone. (9) Acids which may be employed include organic acids such as acetic acid, propionic acid and the like. Solvents which can be employed for the oxidation reaction include methylene chloride, chloroform and the like. The reaction can be carried out at a temperature between 0° C. and room temperature. The ketone (9) can also be obtained by acid hydrolysis of the ketal (4). Acids which can be employed include organic acids such as acetic acid, propionic acid and the like. Removal of the t-butyldiphenylsilyl group from the ketone (8) with an inorganic fluoride such as tetra-n-butylammonium fluoride, or potassium fluoride, for example, in a suitable solvent such as tetrahydrofuran affords the bicyclic hemiacetal (10) which is converted to the methyl ether (11) by treatment with trimethylorthoformate or methanol and a catalytic amount of an acid such as sulfuric acid or p-toluenesulfonic acid.

The methyl ether (11) can also be prepared by first protecting the hydroxyl group of the cycloheptanol derivatives (4 or 7) as the acid resistant benzyl ether (22) by reaction of the cycloheptanol derivative with a halide such as benzyl bromide, for example, in a suitable solvent such as tetrahydrofuran-HMPA. The acid labile t-butyldimethylsilyl group can be selectively removed with aqueous acid, such as aqueous acetic acid, to give a cycloheptanol which upon oxidation with an oxidizing agent such as pyridinium chlorochromate, for example, affords the corresponding ketone (23). The ketone (23) can also be obtained by acid hydrolysis of the ketal (22). Debenzylation of the ketone (23) with boron tribromide or iodotrimethylsilane in a suitable solvent, such as methylene chloride, results in the formation of the bicyclic hemiacetal (10) which in turn is converted to the methyl ether (11) by treatment with trimethylorthoformate or anhydrous methanol and a catalytic amount of an acid such as sulfuric acid or p-toluenesulfonic acid.

Alternatively, the methyl ether (11) can be prepared by hydrolysis of the hydroxyketal (4) with an aqueous inorganic acid such as hydrochloric or sulfuric acid or with p-toluenesulfonic acid to give the bicyclic hemiacetal (10) followed by treatment of the reaction product with trimethylorthoformate or anhydrous methanol and a catalytic amount of an acid such as sulfuric acid or p-toluenesulfonic acid. The methyl ether (11) can be prepared directly from the hydroxyketal (4) by treatment with methanol and a catalytic amount of an inorganic acid such as sulfuric acid or hydrochloric acid, or p-toluenesulfonic acid.

Reduction of the nitrile (11) with a reducing agent such as diisobutylaluminum hydride in a suitable solvent such as toluene gives the corresponding aldehyde (12). The reaction is preferably carried out at a temperature between about −80° C. to 0° C. Reaction of the aldehyde (12) with the ylide of triethylphosphonopropionate in a suitable solvent such as tetrahydrofuran (other solvents) affords the α,β-unsaturated ester (13). Catalytic hydrogenation of the ester (13) gives the saturated ester (14). Catalysts which can be employed include palladium on carbon, platinum oxide and the like. Suitable solvents include ethyl acetate, methanol and tetrahydrofuran. The saturated ester (14) is then converted to the corresponding aldehyde (16) either by direct reduction with a reducing agent such as diisobutylaluminumhydride, for example, or by first reducing it with a reducing agent such as lithium aluminum hydride to the carbinol (15) which is then oxidized with a suitable oxidizing agent such as pyridinium chlorochromate. Suitable solvents for the reduction include tetrahydrofuran, toluene and hexane. Suitable solvents for the oxidation include methylene chloride, chloroform and the like.

The Grignard reaction of 3-methyl-3-butenylmagnesium bromide with the aldehyde (16) gives the secondary alcohol (17) which is protected as its ester (18) by treatment with a lower alkanoic anhydride such as acetic anhydride, propionic anhydride, butyric anhydride, valeric anhydride and the like, an alkanoic acid halide such as acetyl chloride or propionyl chloride or an aroyl acid halide such as benzoyl chloride in the presence of a base such as pyridine. The terminal double bond in the long side chain is isomerized to the more stable isopropylidene moiety (19) by reaction with an acid such as tosic acid or camphorsulfonic acid, for example, in a suitable solvent such as benzene, toluene, or xylene. The reaction is preferably carried out at the reflux temperature of the solvent. Removal of the methyl acetal group with dilute inorganic acid such as hydrochloric acid, for example, gives the hemiacetal (20) which is condensed with (carbethoxyethylidene)-triphenylphosphorane to afford the diester (21). The condensation reaction is preferably carried out at a temperature between about 80° C. to 150° C. Hydrolysis of the diester with alcoholic base, such as sodium hydroxide in methanol, for example, gives the racemic acid (IA and IB). The compounds can be separated by gas chromatography of their di-trimethylsilyl derivatives. The cycloheptane compounds are active uteroevacuant agents. The compounds are effective in interrupting pregnancy at dosage levels between about 20 mg/kg and 400 mg/kg. The actual dosage employed will depend upon the species of animal to which the compound is administered. The compounds can be administered in formulations prepared according to acceptable pharmaceutical practices. Suitable formulations would include solutions, suspensions and solid dosage forms in pharmaceutically acceptable carriers. The compounds can be administered orally or in any conventional manner in accordance with acceptable pharmaceutical practices.

The following examples describe the invention in greater particularity and are intended to be a way of illustrating but not limiting the invention.

EXAMPLE 1

($\pm$) 5-Ethylenedioxy-2-methylcycloheptanone (2-a)

An ether solution of diazoethane is prepared as follows: N-ethyl-N-nitrosourea (70 g, 0.6 mol) is added in small portions to a cooled ($-10°$ C.) stirred mixture of ether (500 ml) and 50% aq. KOH (100 ml) in a 1 liter Erlenmeyer flask over a period of 1 hour. The mixture is stirred for an additional 0.3 hours at $-10°$ C. and the yellow ether layer containing diazoethane is decanted. The aqueous layer is stirred at $-10°$ C. with additional ether (100 ml) for 15 minutes and then decanted. The combined ether phase ($\sim$540 ml) is dried for 0.5 hours with KOH pellets ($\sim$25 g). The molarity of the diazoethane solution (0.235 M) is determined by titration of an aliquot (2$\times$5 ml) with a known weight of excess benzoic acid which in turn is back titrated with 0.1 N NaOH.

To this diazoethane solution (530 ml, 0.124 mol) at $-10°$ C. is added a solution of 4-ethylenedioxy-2-methylcyclohexanone (15.48 g, 0.099 mol) in ethanol (353 ml) over a period of $\sim$10 minutes. The cooling bath is removed and the solution is stirred at room temperature for 2 hours. Excess diazoethane is decomposed by adding acetic acid. Removal of the solvent in vacuo affords a liquid (18.4 g) containing ($\pm$) 5-ethylenedioxy-2-methylcycloheptanone as the major component.

A portion of the crude product (5.8 g) is applied to a column of silica gel (300 g). The desired product ($\pm$) 5-ethylenedioxy-2-methylcycloheptanone (2.1 g) is eluted with 2% ethyl acetate/$CH_2Cl_2$. NMR ($CDCl_3$)$\delta$: 1.10 (d, J=7 Hz, 3H, 2—C$\underline{H}_3$), 3.95 (s, 4, O—C$\underline{H}_2$—C$\underline{H}_2$O Ir (neat)$\mu$: 5.87 (C=O), 9.14 (C—O—C); GC/ms: One major component is observed in the RGC. m/e: 184 ($M^+$).

EXAMPLE 2

($\pm$) 5-Hydroxy-2-methylcycloheptanone (2-b)

To a freshly prepared solution of diazoethane in ether ($\sim$550 ml of 0.297 M=163 mmol) cooled to $-10°$ C. and well stirred with a magnetic stirrer in an open 1 liter Erlenmeyer flask is added slowly a solution of 4-hydroxycyclohexanone (14.8 g, 13 mmol) in ethanol (150 ml) over a period of 15 minutes. The cooling bath is removed and the stirred reaction mixture is allowed to come to room temperature and stirred overnight. The excess diazoethane is discharged by adding a few drops of 10% aq. acetic acid and then the solvent is removed in vacuo. The residue is dissolved in ether, washed with a satd. aq. $NaHCO_3$ solution, dried ($Na_2SO_4$) and the ether is removed in vacuo. Distillation of the residue in vacuo affords ($\pm$) 5-hydroxy-2-methylcycloheptanone which exists as an equilibrium mixture with its tautomeric bicyclic hemiacetal form (bp, 1.4 mm, 97°–99°, 17.51 g, 95%). IR (neat)$\mu$: 2.93 (OH), 5.90 (C=O); NMR ($CDCl_3$)$\delta$: 0.91 (d, J=7 Hz, 2-CH of 2-y), 1.08 (d, J=7 Hz, 2—C$\underline{H}_3$), 3.4–4.5 (m, H—C<—OH and H—C<—O—C); GC-MS: RGC shows two components ($\sim$60:40) both of which show $M^+$ 142 and identical fragmentations. MOX derivatization gave a single peak in RGC with $M^+$ 171.

EXAMPLE 3

($\pm$) 2-(2'-Cyanoethyl)-5-ethylenedioxy-2-methylcycloheptanone (3)

To a stirred solution of ($\pm$) 5-ethylenedioxy-2-methylcycloheptanone (18.0 g, 98 mmol) in dimethoxyethane (30 ml) at $-10°$ C. is added 30% KOH/methanol (1.5 ml) followed by acrylonitrile (10.39 g, 196 mmol). The solution is stirred overnight at room temperature, diluted with ether (300 ml), and washed with distilled water and brine. The organic phase is dried ($Na_2SO_4$), filtered, and the solvent removed in vacuo to afford a yellow solid (23.6 g) containing ($\pm$) 2-(2'-cyanoethyl)-5-ethylenedioxy-2-methyl-cycloheptanone as the major product. A second similar reaction using crude 5-ethylenedioxy-2-methylcycloheptanone (16.5 g) affords additional crude product (22.7 g). The combined crude product (46.3 g) is applied to a column of silica gel (2 kg) and eluted with increasing gradients of ethyl acetate/hexane. The desired cycloheptanone is eluted with $\sim$30% ethyl acetate/hexane (21.3 g, 55%). Recrystallization of the cycloheptanone (4 g) from ether/hexane affords ($\pm$) 2-(2'-cyanoethyl)-5-ethylenedioxy-2-methyl-cycloheptanone (2.29 g) as a white crystalline solid, mp 58°–60°. NMR (CDCl$_3$)δ: 1.08 (s, 3, 2—C$\underline{H}_3$), 3.88 (s, 4, O—C$\underline{H}_2$—C$\underline{H}_2$—O—); IR (neat)μ: 4.47 (C≡N), 5.90 (C=O), 9.05 (C—O—C); GC/MS: One major fraction is observed in the RGC. m/e. 237 (M+).

EXAMPLE 4

(±) 1S,2R-2-(2'-Cyanoethyl)-5-ethylenedioxy-2-methylcycloheptan-1-ol (4-A)

Sodium borohydride (7.13 g, 10 equiv.) is added to a stirred solution of (±) 2-(2'-cyanoethyl)-5-ethylenedioxy-2-methyl-cycloheptanone (16.4 g) in methanol (400 ml) at 0° C. under nitrogen over a 15 minute period. The cooling bath is removed and the solution is stirred overnight at room temperature. The solvent is removed in vacuo and the residue is treated with satd. NH$_4$Cl solution and extracted with CH$_2$Cl$_2$. The combined organic phase is washed (brine), dried (Na$_2$SO$_4$), filtered, and evaporated in vacuo to afford a white crystalline solid mixture (13.7 g). The mixture is recrystallized from ether to afford a solid (4.6 g, 28%, mp 66°–68°), which is mainly the trans alcohol (~95% by nmr) (±) 1S,2R-2-(2'-cyanoethyl)-5-ethylenedioxy-2-methylcycloheptan-1-ol. The pure alcohol is obtained by several recrystallizations from ether, mp 68°–70° C. NMR (CDCl$_3$)δ: 0.97 (s, 3, 2—C$\underline{H}_3$), 3.47 (m, 1, 1-H), 3.88 (s, 4, O—C$\underline{H}_2$C$\underline{H}_2$—O—), IR (neat)μ: 2.88 (OH) 4.45 (C≡N); GC/MS: The RGC consists of one major fraction. m/e: 221 (M+—H$_2$O).

EXAMPLE 5

(±) 1R,2R-2-(2'-Cyanoethyl)-5-ethylenedioxy-2-methylcycloheptan-1-ol (4-B)

Following the isolation of (±) 1S,2R-2-(2'-cyanoethyl)-5-ethylenedioxy-2-methylcycloheptan-1-ol from a mixture of (±) 1S,2R-2-(2'-cyanoethyl)-5-ethylenedioxy-2-methylcycloheptan-1-ol and (±) 1R,2R-2-(2'-cyanoethyl)-5-ethylenedioxy-2-methylcycloheptan-1-ol by column chromatography on silica gel with 35% ethyl acetate/cyclohexane, further elution with 35–50% ethyl acetate/cyclohexane gives the cis isomer (±) 1R,2R-2-(2'-cyanoethyl)-5-ethylenedioxy-2-methylcycloheptan-1-ol, mp 78°–79° C. IR (KBr)μ: 2.86 (OH), 4.46 (C≡N); NMR (CDCl$_3$)δ: 0.93 (s 3H, 2—C$\underline{H}_3$), 4.33 (m, 1H, 1-H), 3.92 (s, 4H, —OC$\underline{H}_2$—C$\underline{H}_2$—O).

EXAMPLE 6

(±) 2-(2'-Cyanoethyl)-2-methyl-5-t-butyldimethylsilyloxycycloheptanone (6)

Substituting (±) 2-methyl-5-t-butyldimethylsilyloxycycloheptanone for (±) 5-ethylenedioxy-2-methylcycloheptanone in the procedure for the preparation of (±) 2-(2'-cyanoethyl)-5-ethylenedioxy-2-methylcycloheptanone, there is obtained (±) 2-(2'-cyanoethyl)-2-methyl-5-t-butyldimethylsilyloxycycloheptanone. IR (neat)μ: 4.42 (C≡N), 5.9 (C=O); NMR (CDCl$_3$-CHCl$_3$ as ref. at 436 Hz)δ: 0.1 [S, 6H, OSi(C$\underline{H}_3$)$_2$], 0.93 [s, 9H, OSi(CH$_3$)$_2$—C(C$\underline{H}_3$)$_3$], 1.13 (s, 3H, 2—C$\underline{H}_3$), 3.95 (bm, 1H, 5-H); MS: 294 (M+—CH$_3$).

EXAMPLE 7

(±) 1S,2R and (±) 1R,2R-2-(2'-Cyanoethyl)-2-methyl-5-t-butyldimethylsilyloxycycloheptan-1-ol (7-A and 7-B)

Substituting (±) 2-(2'-cyanoethyl)-2-methyl-5-t-butyldimethylsilyloxycycloheptanone for (±) 2-(2'-cyanoethyl)-5-ethylenedioxy-2-methylcycloheptanone in the procedure for the preparation of (±) 1S,2R-2-(2'-cyanoethyl)-5-ethylenedioxy-2-methylcycloheptan-1-ol a mixture of isomers is obtained which can be separated by chromatography on silica gel to give (±) 1S,2R and 1R,2R-2-(2'-cyanoethyl)-2-methyl-5-t-butyldimethylsilyloxycycloheptan-1-ol.

EXAMPLE 8

(±) 5-t-Butyldimethylsilyloxy-2-methylcycloheptanone (5)

Imidazole (2.45 g, 31.6 mmol) is added to a solution of (±) 5-hydroxy-2-methylcycloheptanone (2.03 g, 14.3 mmol) in dimethylformamide (35 ml) at 0° C. followed by t-butyldimethylsilyl chloride (2.38 g, 15.7 mmol) under nitrogen. The mixture is stirred at room temperature for 17 hours and then diluted with ether (100 ml) and washed three times with water. After drying (Na$_2$SO$_4$), the ether is removed in vacuo to afford (±) 5-t-butyldimethylsilyloxy-2-methylcycloheptanone (3.7 g, 100%). IR (neat)μ: 5.88 (C=O); NMR (CDCl$_3$)δ: 0.1 (s, 6H, Si(C$\underline{H}_3$)0.93 [s, 9H, Si(CH$_3$)$_2$—C(C$\underline{H}_3$)$_3$], 1.1 (d, J=2—C$\underline{H}_3$), 3.6–4.2 (m, 1H, 5-H).

EXAMPLE 9

(±) 1S,4S,5R-5-(2'-Cyanoethyl)-5-methyl-8-oxabicyclo[3.2.1]octan-1-ol (10-B)

To a stirred solution of (±) 2-(2'-cyanoethyl)-5-ethylenedioxy-2-methylcycloheptan-1-ol (6.5 g, 27 mmol), in acetone (50 ml) is added conc. HCl (0.25 ml) under nitrogen. The solution is refluxed for 1 hour and stirred at room temperature for 4 hours. The acetone is removed in vacuo. The residue is dissolved in ethyl acetate (300 ml), washed (NaHCO$_3$, brine), dried (Na$_2$SO$_4$), and the solvent removed in vacuo to afford crude product (5.3 g, ~100%). A portion of this (1.0 g) is recrystallized (ether) to give 0.31 g of recrystallized product (31%), mp 102°–103°. A second recrystallization (ether) gives analytically pure (±) 1S,4S,5R-5-(2'-cyanoethyl)-5-methyl-8-oxabicyclo[3.2.1]octan-1-ol (0.18 g, mp 104°–105°). NMR (CDCl$_3$)δ: 0.82 (s, 3H, 5—C$\underline{H}_3$), 3.83 (m, 1H, 4-H); IR (KBr)μ: 2.87 (OH), 4.44 (C≡N); GC/MS: One major component, m/e: 195 (M+).

EXAMPLE 10

(±) 1R,4R,5R-5-(2'-Cyanoethyl)-5-methyl-8-oxabicyclo[3.2.1]octan-1-ol (10-A)

Substituting (±) 1R,2R-2-(2'-cyanoethyl)-5-ethylenedioxy-2-methylcycloheptan-1-ol for (±) 1S,2R-2-(2'-cyanoethyl)-5-ethylenedioxy-2-methylcycloheptan-1-ol in the procedure for the preparation of (±) 1S,4S,5R-5-(2'-cyanoethyl)-5-methyl-8-oxabicyclo[3.2.1]octan-1-ol there is obtained (±) 1R,4R,5R-5-(2'-cyanoethyl)-5-methyl-8-oxabicyclo[3.2.1]octan-1-ol. IR (KBr)μ: 2.86 (OH), 4.45 (C≡N); NMR (CDCl$_3$)δ: 1.12 (S, 3H, 5—C$\underline{H}_3$), 3.85 (m, 1H, 4-H); m/e: 195 (M+).

EXAMPLE 11

(±)
1S,4S,5R-5-(2'-Cyanoethyl)-5-methyl-8-oxabicyclo[3.2.1]octan-1-ol methyl ether (11-B)

Methanolic sulfuric acid (0.4 ml of 0.2 N sulfuric acid in methanol) is added to a solution of (±) 1S,4S,5R-5-(2'-cyanoethyl)-5-methyl-8-oxabicyclo[3.2.1]-octan-1-ol (85 mg, 4.36 mmol) in methyl orthoformate (0.7 ml, large excess) and the mixture is stirred at room temperature under nitrogen for 17 hours. The reaction mixture is treated with excess 10% aq. NaHCO$_3$ solution and then taken to dryness on a rotary evaporator. The residue is partitioned between water and methylene chloride and the separated organic layer is washed with brine, dried (K$_2$CO$_3$) and evaporated to dryness to afford (±) 1S,4S,5R-5-(2'-cyanoethyl)-5-methyl-8-oxabicyclo[3.2.1]-octan-1-ol methyl ether (79 mg). IR (neat)μ: 4.46 (C≡N); NMR (CDCl$_3$)δ: 0.82 (s, 3H, 5—CH$_3$), 3.38 (s, 3H, OCH$_3$), 3.85 (m, 1H, 4-H); 209 (M+).

EXAMPLE 12

(±)
1R,4R,5R-5-(2'-Cyanoethyl)-5-methyl-8-oxabicyclo[3.2.1]octan-1-ol methyl ether (11-A)

Substituting (±) 1R,4R,5R-5-(2'-cyanoethyl)-5-methyl-8-oxabicyclo[3.2.1]octan-1-ol for (±) 1S,4S,5R-5-(2'-cyanoethyl)-5-methyl-8-oxabicyclo[3.2.1]octan-1-ol in the procedure for the preparation of (±) 1S,4S,5R-5-(2'-cyanoethyl)-5-methyl-8-oxabicyclo[3.2.1]octan-1-ol methyl ether there is obtained (±) 1R,4R,5R-5-(2'-cyanoethyl)-5-methyl-8-oxabicyclo[3.2.1]octan-1-ol methyl ether. IR (neat)μ: 4.45 (C≡N); NMR (CDCl$_3$)δ: 1.12 (s, 3H, 5—CH$_3$), 3.40 (s, 3H, —OCH$_3$), 3.87 (m, 1H, 4-H); m/e: 209 (M+).

EXAMPLE 13

(±)
1S,2R-2-(2'-Cyanoethyl)-5-ethylenedioxy-2-methyl-1-t-butyldiphenylsilyloxycycloheptane (8-B)

By substituting (±) 1S,2R-2-(2'-cyanoethyl)-5-ethylenedioxy-2-methylcycloheptan-1-ol for (±) 5-hydroxy-2-methylcycloheptanone and t-butyldiphenylsilyl chloride for t-butyldimethylsilyl chloride in the procedure for the preparation of 5-t-butyldimethylsilyloxy-2-methylcycloheptanone, (±) 1S,2R-2-(2'-cyanoethyl)-5-ethylenedioxy-2-methyl-1-t-butyldiphenylsilyloxycycloheptanone is obtained after purification of the crude product by chromatography on silica gel (8–16% ethyl acetate/cyclohexane). IR (KBr)μ: 4.46 (C≡N); NMR (CDCl$_3$)δ: 0.98 (s, 3H, 2—CH$_3$), 11.06 [s, 9H, Si—C—(CH$_3$)$_3$], 3.38 (bm, 1H, 1-H), 3.73 (s, 4H, —O—(CH$_2$)$_2$—O—), 7.2–7.8 (m, 10H, ArH); m/e: 420 (M+-57).

EXAMPLE 14

(±) 1S,2R and
1R,2R-2-(2'-Cyanoethyl)-2-methyl-5-t-butyldimethylsilyloxy-1-t-butyldiphenylsilyloxycycloheptane [8-(A+B)]

By substituting (±) 1S,2R and (±) 1R,2R-2-(2'-cyanoethyl)-2-methyl-5-t-butyldimethylsilyloxycycloheptan-1-ol for (±) 1S,4S,5R-5-(2'-cyanoethyl)-5-methyl-8-oxabicyclo[3.2.1]octan-1-ol in the procedure for the preparation of (±) 1S,2R-2-(2'-cyanoethyl)-5-ethylenedioxy-2-methyl-1-t-butyl-diphenylsilyloxycycloheptane, there is obtained (±) 1S,2R and (±) 1R,2R-2-(2'-cyanoethyl)-2-methyl-5-t-butyldimethylsilyloxy-1-t-butyldiphenylsilyloxycycloheptane.

EXAMPLE 15

(±) 4R,5R and (±)
4S,5R-5-(2'-cyanoethyl)-5-methyl-4-t-butyldiphenylsilyloxycycloheptan-1-one [9-(A+B)]

The ketal (±) 1S,2R and (±) 1R,2R-2-(2'-cyanoethyl)-5-ethylenedioxy-2-methyl-5-t-butyldiphenylsilyloxycycloheptane (0.489 g) in tetrahydrofuran (5 ml) is treated with 80% aq. acetic acid (5 ml) at room temperature for 12 hours. Evaporating the mixture to dryness in vacuo gives the ketone (±) 4R,5R and (±) 4S,5R-5-(2'-cyanoethyl)-5-methyl-4-t-butyldiphenylsilyloxy-cycloheptan-1-one.

Alternatively, similar treatment of (±) 1S,4R and (±) 1R,2R-2-(2'-cyanoethyl)-2-methyl-5-t-butyldimethylsilyloxy-1-t-butyldiphenylsilyloxycycloheptane with aq. acetic acid followed by oxidation of the crude inermediate cycloheptanol with pyridinium chlorochromate in CH$_2$Cl$_2$ according to the procedure described for the preparation of (±) 1R,4R,5R(cis) and (±) 1S,4S,5R-(trans)-5-(5'-oxo-4'-methylpentyl)-5-methyl-8-oxabicyclo[3.2.1]-octan-1-ol methyl ether from (±) 1R,4R,5R(cis) and (±) 1S,4S,5R(trans)-5-(5'-hydroxy-4'-methylpentyl)-5-methyl-8-oxabicyclo[3.2.1]octan-1-ol methyl ether gives (±) 4R,5R and (±) 4S,5R-5-(2'-cyanoethyl)-5-methyl-4-t-butyldiphenylsilyloxycycloheptan-1-one.

EXAMPLE 16

(±) 1R,4R,5R and (±)
1S,4S,5R-5-(2'-cyanoethyl)-5-methyl-8-oxabicyclo[3.2.1]octan-1-ol [11-(A+B)]

A solution of (±) 4R,5R and (±) 4S,5R-5-(2'-cyanoethyl)-5-methyl-4-t-butyldiphenylsilyloxycycloheptan-1-one (0.443 g) in tetrahydrofuran (5 ml) is treated with a 1 M solution of tetra-n-butylammonium fluoride (2 mmol) in tetrahydrofuran for 5 hours at room temperature. Dilution with H$_2$O and extraction with CH$_2$Cl$_2$ followed by the removal of the solvent in vacuo gives (±) 1R,4R,5R and (±) 1S,4S,5R-5-(2'-cyanoethyl)-5-methyl-8-oxabicyclo[3.2.1]octan-1-ol.

EXAMPLE 17

(±)
1S,2R,1-Benzyloxy-2-(2'-cyanoethyl)-5-ethylenedioxy-2-methylcycloheptane (23-B)

To a suspension of sodium hydride (2.24 g, 50% oil dispersion, 46 mmol, washed with hexane, 3×10 ml) in tetrahydrofuran (10 ml) and HMPA (8.1 ml, 46 mmol) is added a solution of (±) 1S,4S,5R-5-(2'-cyanoethyl)-5-methyl-8-methyl-8-oxabicyclo[3.2.1]octan-1-ol (5.57 g, 23 mmol) in tetrahydrofuran (50 ml) at room temperature under nitrogen with cooling. After stirring for 17 hours (n-C$_4$H$_9$)$_4$NI (3.44 g, 9.3 mmol) and benzylbromide (3.3 ml, 28 mmol) are added. The mixture is stirred for 4 hours, diluted with ether (100 ml), washed with H$_2$O (150 ml) and the aqueous phase extracted with ether (3×100 ml). The combined ether extracts are washed (brine), dried (Na$_2$SO$_4$), filtered, and concentrated in vacuo to afford a crude product (9.0 g) which is applied to a column of silica gel (200 g, Baker). The purified benzyl ether (±) 1S,2R,1-benzyloxy-2-(2'-cyanoethyl)-5-ethylenedioxy-2-methylcycloheptane (4.4 g, 57%) is eluted with 15% ethyl acetate/hexane plus 0.1% pyridine (250 ml frac.). NMR (CDCl$_3$)δ: 0.97 (s, 3H, 2—C$\underline{H}_3$), 3.13 (m, 1H, 1-H), 3.88 (s, 4H, O—C$\underline{H}_2$C$\underline{H}_2$—O), 4.43 (ABq, J=12 Hz, 2H, O—C$\underline{H}_2$—φ), 7.35 (s, 5H, Ar-H); IR (neat)μ: 4.50 (C≡N), 9.22 (C—O—C); GC/MS: The RGC consists of one major fraction whose spectrum corresponds to the benzyl ketal. m/e: 329 (M+).

EXAMPLE 18

(±) 1R,2R,1-Benzyloxy-2-(2'-cyanoethyl)-5-ethylenedioxy-2-methylcycloheptane (22-A)

To a suspension of sodium hydride (1.15 g, 50% oil dispersion, 24 mmol, washed with hexane and tetrahydrofuran, 1×10 ml each) in tetrahydrofuran (2 ml) under nitrogen at 5° C., is added a solution of (±) 1R,2R-2-(2'-cyanoethyl)-5-ethylenedioxy-2-methylcycloheptan-1-ol (2.9 g, 12 mmol) in tetrahydrofuran (20 ml) followed by HMPA (4.2 ml, 24 mmol). The mixture is stirred for 2 hours at room temperature and then (n-C$_4$H$_9$)$_4$NI (0.89 g, 20 mmol) and benzyl bromide (1.71 ml, 14 mmol) are added. The mixture is stirred at room temperature for 17 hours, diluted with ether (200 ml), washed with H$_2$O (150 ml) and the aqueous phase extracted with ether (3×100 ml). The combined ether extracts are washed (brine), dried (Na$_2$SO$_4$), filtered and concentrated in vacuo to afford the crude product (8.0 g) which is purified by column chromatography (silica gel, 200 g, 15% ethyl acetate/hexane) to afford (±) 1R,2R,1-benzyloxy-2-(2'-cyanoethyl)-5-ethylenedioxy-2-methylcycloheptane (3.053 g, 77%) as a colorless oil. NMR (CDCl$_3$)δ: 0.95 (s, 3H, 2—C$\underline{H}_3$), 3.08 (m, 1H, 1-H), 3.88 (s, 4H, OC$\underline{H}_2$C$\underline{H}_2$O), 4.47 (ABq, J=12 Hz, 2H, φ—C$\underline{H}_2$—O), 7.32 (s, 5H, Ar-H); IR (neat)μ: 4.45 (C≡N), 9.22 (COC); GC/MS: The RGC consists of one major fraction having an MH+ 330 using methane as the reagent gas (CI).

EXAMPLE 19

(±) 4S,5R and (±) 4R,5R-5-(2'-Cyanoethyl)-5-methyl-4-benzyloxycyclohept-1-one [23-(A+B)]

By substituting (±) 1R,2R and (±) 1S,2R-1-benzyloxy-2-(2'-cyanoethyl)-5-ethylenedioxy-2-methylcycloheptane for (±) 1S,2R and (±) 1R,2R-2-(2'-cyanoethyl)-5-ethylene-dioxy-2-methyl-5-t-butyldiphenylsilyloxycycloheptane in the procedure for the preparation of (±) 4R,5R and (±) 4S,5R-5-(2'cyanoethyl)-5-methyl-4-t-butyldiphenylsilyloxycycloheptan-1-one, there is obtained (±) 4S,5R and (±) 4R,5R-5-(2'-cyanoethyl)-5-methyl-4-benzyloxy cyclohept-1-one. Similarly by substituting (±) 1R,2R and (±) 1S,2R-1-benzyloxy-2-(2'-cyanoethyl)-5-t-butyldimethylsilyloxy-2-methylcycloheptane for (±) 1S,2R and (±) 1R,2R-2-(2'-cyanoethyl)-2-methyl-5-t-butyldimethylsilyloxy-1-t-butyldiphenylsilyoxycycloheptane in the alternative procedure for the preparation of (±) 4R,5R and (±) 4S,5R-(2'-cyanoethyl)-5-methyl-4-t-butyldiphenylsilyloxycycloheptan-1-one, there is obtained (±) 4S,5R and (±) 4R,5R-5-(2'-cyanoethyl)-5-methyl-4-benzyloxycyclohept-1-one.

EXAMPLE 20

(±) 1R,4R,5R and (±) 1R,4R,5S-5-(2'-Cyanoethyl)-5-methyl-8-oxabicyclo[3.2.1]octan-1-ol [10-(A+B)]

A solution of (±) 4S,5R and (±) 4R,5R-5-(2'-cyanoethyl)-5-methyl-4-benzyloxycyclohept-1-one (0.284 g) in methylene chloride (2 ml) at 0° C. is treated with boron tribromide (0.752 g) for 2 hours. Dilution with water and extraction with CH$_2$Cl$_2$ gives, after the removal of the solvent, (±) 1R,4R,5R and (±) 1R,4R,5S-5-(2'-cyanoethyl)-5-methyl-8-oxabicyclo[3.2.1]octan-1-ol.

EXAMPLE 21

(±) 1R,4R,5R and (±) 1S,4S,5R-5-(2'-Cyanoethyl)-5-methyl-8-oxabicyclo[3.2.1]octan-1-ol methyl ether [11-(A+B)]

A 30:70 mixture of alcohols (±) 1S,2R-2-(2'-cyanoethyl)-5-ethylenedioxy-2-methylcycloheptan-1-ol and (±) 1R,2R-2(2'-cyanoethyl)-5-ethylenedioxy-2-methylcycloheptan-1-ol (16.2 g, 68 mmol) is dissolved in 0.3% H$_2$SO$_4$/methanol (300 ml) and stirred for 4 hours at room temperature under nitrogen. The solution is poured into cold 10% NaHCO$_3$ (100 ml) and the methanol removed in vacuo. The aqueous phase is extracted with CH$_2$Cl$_2$ (6×100 ml). The combined CH$_2$Cl$_2$ extracts are washed (brine), dried (Na$_2$SO$_4$), filtered and concentrated in vacuo to afford (±) 1R,4R,5R and (±) 1S,4S,5R-5-(2'-cyanoethyl)-5-methyl-8-oxabicyclo[3.2.1]octan-1-ol methyl ether as a colorless oil (12.6 g, 89%). NMR (CDCl$_3$)δ: 0.83, 1.10 (s, each, 3H, 5—C$\underline{H}_3$, 70:30 trans:cis, resp.), 3.37 (3, 3H, O—C$\underline{H}_3$), 3.82 (m, 1H, 4-H); IR (neat)μ: 4.46 (C≡N); GC/MS: One major component m/e 209 (M+).

EXAMPLE 22

(±) 1R,4R,5R and (±) 1S,4S,5R-5-Methyl-5-(3'-oxopropyl)-8-oxabicyclo[3.2.1]octan-1-ol methyl ether [12-(A+B)]

Diisobutylaluminum hydride (1.4 M/toluene, 53 ml, 76 mmol) is added to (±) 1R,4R,5R and (±) 1S,4S,5S-5-(2'-cyanoethyl)-5-methyl-8-oxabicyclo[3.2.1]octan-lol methyl ether (12.2 g, 59 mmol) in toluene (250 ml) under nitrogen at −80° C. over a 15 minute period. The solution is stirred at room temperature for 2 hours and then refluxed with H$_2$O (150 ml) for 1 hour. The mixture is extracted with CHCl$_3$ (5×200 ml), washed (brine), dried (Na$_2$SO$_4$), filtered in vacuo, and concentrated to afford the crude product as a yellow oil (14 g, crude >100%) which is purified by column chromatography (silica gel, 300 g). Elution with 15% ethyl acetate/hexane affords (±) 1R,4R,5R and (±) 1S,4S,5R-5-methyl-5-(3'-oxopropyl)-8-oxabicyclo[3.2.1]octan-1-ol-methyl ether as a colorless oil (7.0 g, 56%). NMR (CDCl$_3$)δ: 0.75, 1.05 (s, each, 3H each, 5—C$\underline{H}_3$), 3.35 (s, 3H, OC$\underline{H}_3$), 3.82 (m, 3H, 4-H), 11.0 (d, J=2 Hz, 1H, C$\underline{H}$O); IR (neat)μ: 3.68 (CHO), 5.80 (C═O); GC/MS: One major component, m/e 212 (M+).

EXAMPLE 23

(±) 1R,4R,5R and (±) 1S,4S,5R-5-(4'-Ethoxycarbonyl-3'-pentenyl)-5-methyl-8-oxabicyclo[3.2.1]octan-1-ol methyl ether [13-(A+B)]

Triethyl-α-phosphonopropionate (11.78 g, 50 mmol) is added to sodium hydride (1.78 g, 74 mmol, 2.25 eq., 50% oil dissersion, washed with hexane, 2×20 ml) in tetrahydrofuran (5 ml) at 0° C. under nitrogen. The mixture is stirred for 1 hour at room temperature and aldehyde (±) 1R,4R,5R and (±) 1S,4S,5R-5-methyl-5-(3'-oxopropyl)8-oxabicyclo[3.2.1]octan-1-ol methyl ether (7.0 g, 33 mmol) is added with cooling (ice-bath). The mixture is stirred for 1 hour at room temperature, refluxed for 1 hour, treated with H$_2$O (40 ml), and extracted with ether (3×100 ml). The combined ether extracts are washed (brine), dried (Na$_2$SO$_4$), filtered and concentrated in vacuo to afford (±) 1R,4R,5R and (±) 1S,4S,5R-5-(4'-ethoxycarbonyl-1-3'-pentenyl)-5-methyl-8-oxabicyclo[3.2.1]octan-1-ol methyl ether as a light yellow oil (10 g crude ~100%), which is used in the next step without further purification. NMR (CDCl$_3$)δ: 0.82, 1.12 (s, each, 3H each, 5-C$\underline{H}$$_3$), 1.30 (t, J=7 Hz, 3H, C$\underline{H}$$_3$-CH$_2$), 1.85 (s, 3H, 4'-C$\underline{H}$$_3$), 3.38 (s, 3H, OC$\underline{H}$$_3$), 3.82 (m, 1H, 4-H), 4.17 (q, J=7 Hz, 2H, C$\underline{H}$$_2$CH$_3$), 6.70 (m, 1H, 3'-H, trans); IR (neat)$_\mu$: 5.85 (C=O), 6.10 (C=C); GC/MS: One major component, m/e 296 (M+).

EXAMPLE 24

(±) 1R,4R,5R and (±) 1S,4S,5R-5-(4'-Ethoxycarbonylpentyl)-5-methyl-8-oxabicyclo[3.2.1]octan-1-ol methyl ether [14-(A+B)]

The ester (±) 1R,4R,5R and (±) 1S,4S,5R-5-(4'-ethoxycarbonyl-3'-pentenyl)-5-methyl-8-oxabicyclo[3.2.1]octan-1-ol methyl ether (10 g crude, 33 mmol) in ethyl acetate (200 ml) is hydrogenated (1 atm) over 5% Pd/C (6 eq.) for 3 hours. The mixture is filtered through celite and concentrated in vacuo to afford the crude product which is purified by column chromatography (silica gel, 150 g, 5–10% ethyl acetate/hexane) to afford purified (±) 1R,4R,5R and (±) 1S,4S,5R-5-(4'-ethoxycarbonylpentyl-5-methyl-8-oxabicyclo[3.2.1]octan-1-ol methyl ether 8.4 g, 85%). NMR (CDCl$_3$)δ: 0.73, 1.05 (s, each, 3H each, 5-C$\underline{H}$$_3$), 1.23 (t, J=7 Hz, 3H, C$\underline{H}$$_3$CH$_2$), 3.35 (s, 3H, OC$\underline{H}$$_3$), 3.82 (m, 1H, 4-H), 4.10 (q, J=7 Hz, 2H, CH$_3$C$\underline{H}$$_2$O); IR (neat)$_\mu$: 5.76 (C=O).

EXAMPLE 25

(±) 1R,4R,5R and (±) 1S,4S,5R-5-(5'-hydroxy-4'-methylpentyl)-5-methyl-8-oxabicyclo[3.2.1]octan-1-ol methyl ether [15-(A+B)]

1R,4R,5R and 1S,4S,5R-5-(4'-Ethoxycarbonyl-4'-pentyl-5-methyl-8-oxabicyclo[3.2.1]octan-1-ol methyl ether (7.3 g, 24 mmol) in tetrahydrofuran (100 ml) is added to lithium aluminum hydride (0.93 g, 24 mmol) in tetrahydrofuran (100 ml) under nitrogen over a 15 minute period. The mixture is refluxed for 1 hour, cooled, and then H$_2$O (0.9 ml), 2 N NaOH (0.9 ml), and H$_2$O (2.7 ml) are added successively with cooling. The solution is extracted with ethyl acetate (3×150 ml) and the combined ethyl acetate extracts are washed (satd. NH$_4$Cl soln., brine), dried (Na$_2$SO$_4$), filtered in vacuo and concentrated to afford crude (±) 1R,4R,5R and (±) 1S,4S,5R-5-(5'-hydroxy-4'-methylpentyl)-5-methyl-8-oxabicyclo[3.2.1]octan-1-ol methyl ether (6.4 g, ~100%). NMR (CDCl$_3$)δ: 0.77, 1.07 (s, each, 3H each, 5-C$\underline{H}$$_3$), 0.92 (d, J=7 Hz, 3H, 4'-C$\underline{H}$$_3$), 3.38 (s, 3H, OC$\underline{H}$$_3$), 3.42 (d, J=7 Hz, 2H, 5'-H), 3.87 (m, 1H, 4-H); IR (neat)$_\mu$: 2.90 (OH); GC/MS: One major component, m/e: 256 (M+).

EXAMPLE 26

(±) 1R,4R,5R and (±) 1S,4S,5R-5-(5'-oxo-4'-methylpentyl)-5-methyl-8-oxabicyclo[3.2.1]octan-1-ol methyl ether [16-(A+B)]

The alcohol (±) 1R,4R,5R and (±) 1S,4S,5R-5-(5'-hydroxy-4'-methylpentyl)-5-methyl-8-oxabicyclo[3.2.-1]octan-1-ol methyl ether (3.8 g, 15 mmol) in CH$_2$Cl$_2$ (100 ml) is added to pyridinium chlorochromate (4.8 g, 22 mmol) and sodium acetate (0.36 g, 4 mM) in CH$_2$Cl$_2$ (300 ml) over a 5 minute period at 0° C. The orange mixture turns black upon addition of the alcohol. The mixture is stirred for 1.5 hours at room temperature and filtered through celite. The filtrate is concentrated in vacuo to afford a crude product (3.8 g, 100%) which is passed through a column of silica gel (100 g, 20% ethyl acetate/hexane) to afford the semipurified aldehyde (2.5 g, 66%). This is further purified on a Waters Prep 500 HPLC (8% ethyl acetate/hexane) followed by washing with satd. NaHCO$_3$ to afford pure (±) 1R,4R,5R and (±) 1S,4S,5R-5-(5'-oxo-4'-methylpentyl)-5-methyl-8-oxabicyclo[3.2.1]octan-1-ol methyl ether (2.0 g, 53%). NMR (CDCl$_3$)δ: 0.75, 1.07 (s, each, 3H each, 5-C$\underline{H}$$_3$), 1.08 (d, J=7 Hz, 3H, 4'-C$\underline{H}$$_3$), 3.37 (s, 3H, O-CH$_3$), 3.83 (m, 1H, 4-H), 9.93 (d, J=2 Hz, 1H, 5'-H); IR (neat)$_\mu$: 3.70 (CHO), 5.78 (C=O); GC/MS: One major fraction, m/e (CI, CH$_4$): 255 (MH+).

EXAMPLE 27

(±) 1R,4R,5R and (±) 1S,4S,5R-5-(5'-Hydroxy-4',8'-dimethyl-8'-nonenyl)-5-methyl-8-oxabicyclo[3.2.1]octan-1-ol methyl ether [17-(A+B)]

4-Bromo-3-methyl-1-butene (2.0 g, 13 mmol) in tetrahydrofuran (4 ml) is added to magnesium turnings (0.36 g, 15 mmol) under nitrogen over a 10 minute period. The mixture is heated to 50° C. for 50 minutes. The aldehyde (±) 1R,4R,5R and (±) 1S,4S,5R-5-(5'-oxo-4'-methylpentyl)-5-methyl-8-oxabicyclo[3.2.1]octan-1-ol methyl ether (1.9 g, 7.5 mmol) in tetrahydrofuran (~15 ml) is added at −10° C. over a 10 minute period. The solution is stirred for ~18 hours at room temperature, treated with H$_2$O (5 ml), and extracted with ether (5×150 ml). The combined ether extracts are washed (brine), dried (Na$_2$SO$_4$), filtered, and concentrated in vacuo to afford the alcohol (±) 1R,4R,5R and (±) 1S,4S,5R-5-(5'-hydroxy-4',8'-dimethyl-8'-nonenyl)-5-methyl-8-oxabicyclo[3.2.1]octan-1-ol methyl ether (2.4 g crude, ~100%). NMR (CDCl$_3$)δ: 0.75, 1.07 (s, each, 3H each, 5-C$\underline{H}$$_3$), 0.88 (d, J=7 Hz, 3H, 3H, 4'-C$\underline{H}$$_3$), 3.38 (s, 3H, O-C$\underline{H}$$_3$), 3.42 (m, 1H, 5'-H), 3.87 (m, 1H, 4-H), 4.70 (m, 2H, 9'-H); IR (neat)$_\mu$: 2.88 (OH), 6.08 (C=C); GC/MS: One major component, m/e: 396 (M+, TMS).

EXAMPLE 28

(±) 1R,4R,5R and (±) 1S,4S,5R-5-(5'-Acetoxy-4',8'-dimethyl-8'-nonenyl)-5-methyl-8-oxabicyclo[3.2.1]octan-1-ol methyl ether [18-(A+B)]

The alcohol (±) 1R,4R,5R and (±) 1S,4S,5R-5-(5'-hydroxy-4'-8'-dimethyl-8'-nonenyl)-5-methyl-8-oxabicyclo[3.2.1]octan-1-ol methyl ether (2.4 g, 7 mmol), pyridine (30 ml), and acetic anhydride (10 ml) are stirred at room temperature under nitrogen for 18 hours. The solution is treated with H$_2$O (20 ml), stirred for 30 minutes, and extracted with CH₂Cl₂ (3×100 ml). The combined CH₂Cl₂ extracts are washed (brine), dried (Na₂SO₄), filtered, and concentrated in vacuo to afford a crude product (2.8 g, ~100%) which is purified on a Waters Prep. 500 HPLC (5–10% ethyl acetate/hexane) to afford purified (±) 1R,4R,5R and (±) 1S,4S,5R-5-(5'-acetoxy-4',8'-dimethyl-8'-nonenyl)-5-methyl-8-oxabicyclo[3.2.1]octan-1-ol methyl ether (1.9 g). NMR (CDCl₃)δ: 0.73, 1.05 (s each, 3H each, 5-C$\underline{H}_3$), 0.87 (d, J=7 Hz, 3H, 4'-C$\underline{H}_3$), 2.02 (s, 3H, OCOC$\underline{H}_3$), 3.35 (s, 3H, OC$\underline{H}_3$), 3.82 (m, 1H, 4-H), 4.62 (m, 2H, 9'-H), 4.70 (m, 1H, 5'-H); IR (neat)μ: 5.76 (C=O), 6.06 (C=C); GC/MS: One major component, m/e: 366 (M+).

EXAMPLE 29

(±) 1R,4R,5R and (±) 1S,4S,5R-5-(5'-Acetoxy-4',8'-dimethyl-7'-nonenyl)-5-methyl-8-oxabicyclo[3.2.1]octan-1-ol methyl ether [19-(A+B)]

The alkene (±) 1R,4R,5R and (±) 1S,4S,5R-5-(5'-acetoxy-4',8'-dimethyl-8'-nonenyl)-5-methyl-8-oxabicyclo[3.2.1]octan-1-ol methyl ether (1.9 g, 5 mmol), p-toluenesulfonic acid acid (300 mg), and benzene (100 ml) are refluxed for ~18 hours under nitrogen. The solution is diluted with CH₂Cl₂ (100 ml), washed (satd. NaHCO₃, brine), dried (Na₂SO₄), filtered, and concentrated in vacuo to afford a crude product (2.0 g, 100%) which is purified on a Waters Prep. 500 HPLC (10–20% ethyl acetate/hexane) to afford pure (±) 1R,4R,5R and (±) 1S,4S,5R-5-(5'-acetoxy-4',8'-dimethyl-7'-nonenyl)-5-methyl-8-oxabicyclo[3.2.1]octan-1-ol methyl ether (1.5 g, 80%). NMR (CDCl₃)δ: 0.73, 1.05 (s each, 3H each, 5-C$\underline{H}_3$), 0.88 (d, J=7 Hz, 3H, 3H, 4'-C$\underline{H}_3$), 1.60, 1.68 [s each, 3H each, 8'-(C$\underline{H}_3$)₂], 2.00 (s, 3H, OCOC$\underline{H}_3$), 3.37 (s, 3H, O-C$\underline{H}_3$), 3.82 (m, 1H, 4-H), 4.85 (m, 1H, 5'-H), 5.02 (m, 1H, 7'-H); IR (neat)μ: 5.68 (C=O), 6.10 (C=C); GC/MS: One major component, m/e: 306 [M+-HOAc].

EXAMPLE 30

(±) 1R,4R,5R and (±) 1S,4S,5R-5-(5'-Acetoxy-4',8'-dimethyl-7'-nonenyl)-5-methyl-8-oxabicyclo[3.2.1]octan-1-ol [20-(A+B)]

The methyl ether (±) 1R,4R,5R and (±) 1S,4S,5R-5-(5'-acetoxy-4',8'-dimethy-7'-nonenyl)-5-methyl-8-oxabicyclo[3.2.1]octan-1-ol methyl ether (1.1 g, 3 mmol) in 2 N HCl (1 ml) and acetone (50 ml) are refluxed for 3 hours. The acetone is removed in vacuo and the residue is extracted with ethyl acetate (3×150 ml). The combined ethyl acetate extracts are washed (satd. NaHCO₃, brine), dried (Na₂SO₄), filtered and concentrated, in vacuo to afford (±) 1R,4R,5R and (±) 1S,4S,5R-5-(5'-acetoxy-4',8'-dimethyl-7'-nonenyl)-5-methyl-8-oxabicyclo[3.2.1]octan-1-ol (0.9 g, 82%). NMR (CDCl₃)δ: 0.75, 1.08 (s each, 3H each, 5-CH₃), 0.92 (d, J=7 Hz, 4'-C$\underline{H}_3$), 1.67, 1.73 [s each, 3H each, 8'-C$\underline{H}_3$)₂], 2.05 (s, 3H, OCOC$\underline{H}_3$), 3.85 (m, 1H, 4-H), 4.80 (m, 1H, 5'-H), 5.03 (m, 1H, 7'-H); IR (neat)μ: 2.94 (OH), 5.78 (C=O), 6.06 (C=C); GC/MS: 425 (M+, TMS).

EXAMPLE 31

Ethyl [(±)1R,4R,5R and (±) 1S,4S,5R-5-(5'-acetoxy-4',8'-dimethyl-7'-nonenyl)-5-methyl-8-oxabicyclo[3.2.1]octan-1-yl]acetate [21-(A+B)]

The hemiacetal (±) 1R,4R,5R and (±) 1S,4S,5R-5-(5'-acetoxy-4',8'-dimethyl-7'-nonenyl)-5-methyl-8-oxabicyclo[3.2.1]octan-1-ol (0.85 g, 2.4 mmol) and (carbethoxymethylene)triphenylphosphorane (1.68 g, 4.8 mmol) are heated neat at 150° C. under nitrogen for 48 hours. The dark brown, oily product is purified by column chromatography (silica gel, 75 g). Elution with 30% ethyl acetate/hexane affords ethyl [(±)1R,4R,5R and (±) 1S,4S,5R-5-(5'-acetoxy-4',8'-dimethyl-7'-nonenyl)-5-methyl-8-oxabicyclo[3.2.1]octan-1-yl]acetate (0.76 g, 75%). NMR (CDCl₃)δ: 0.75, 1.05 (s each, 3H each, 5-CH₃), 0.9 (d, J=7 Hz, 3 4'-CH₃), 1.27 (t, J=7 Hz, 3H, CH₂C$\underline{H}_3$), 1.63, 1.70 [s each, 3H each, 8' (C$\underline{H}_3$)₂], 2.02 (s, 3H, O-COC$\underline{H}_3$), 2.63 (s, 2H, C$\underline{H}_2$-COOEt), 3.82 (m, 1H, 4-H), 4.15 (q, J=7 Hz, 2H, C$\underline{H}_2$-CH₃), 4.80 (m, 1H, 5'H), 5.07 (m, 1H, 7'-H); IR (neat)μ: 5.75 (C=O); 6.06 (C=C); GC/MS: One major compound, m/e: 422.

EXAMPLE 32

(±) 1R,4R,5R and (±) 1S,4S,5R-5-(4',8'-Dimethyl-5'-hydroxy-7'-nonenyl)-8-oxabicyclo[3.2.1]octane-1-acetic acid [I-(A+B)]

The ester, ethyl[(±)1R,4R,5R and (±) 1S,4S,5R-5-(5'-acetoxy-4',8'-dimethyl-7'-nonenyl)-5-methyl-8-oxabicyclo[3.2.1]octan-1-yl]acetate (0.86 g), 2 N NaOH (5 ml), and methanol (5 ml) are refluxed for 1 hour under nitrogen. The methanol is removed in vacuo and the residue is diluted with H₂O (distilled, 50 ml). The aqueous phase is extracted with CH₂Cl₂ (2×50 ml). The aqueous alkaline phase is acidified to pH 3 (2 N HCl) and extracted with CH₂Cl₂ (3×100 ml.) The combined CH₂Cl₂ extracts are washed (brine), dried (Na₂SO₄), filtered, and concentrated in vacuo to afford the crude product (0.46 g, 65%). The acidic aqueous phase is re-extracted with ethyl acetate (3×100 ml) and the combined ethyl acetate extracts are washed, dried, filtered, and concentrated to afford additional crude product (0.34 g) which is purified by prep plate chromatography (7% i-propanol/CHCl₃) to afford the crude product (0.24 g, 33%). The combined samples of product (0.70 g) are dissolved in CH₂Cl₂ and filtered in vacuo to afford (±) 1R,4R,5R and (±) 1S,4S,5R-5-(4',8'-dimethyl-5'-hydroxy-7'-nonenyl)-8-oxabi-cyclo[3.2.1]octane-1-acetic acid as a light yellow oil 0.56 g, 78%). NMR (CDCl₃)δ: 0.78, 1.08 (s each, 3H each, 5-C$\underline{H}_3$, 70:30 trans: cis resp.), 0.92 (d, J=7 Hz, 3H, 4'-C$\underline{H}_3$), 1.67, 1.77 [s each, 3H each, 8'-(C$\underline{H}_3$)₂], 2.70 (s, 2H, C$\underline{H}_2$COOH), 3.48 (m, 1H, 5'-H), 3.98 (m, 1H, 4-H), 5.05 (m, 1H, 7'-H); IR (neat)μ: 2.8–4.2 (COOH), 5.83 (C=O), 6.06 (C=C); GC/MS: The di-TMS derivatives of the cis and trans isomers are separated on GC (5'×2 mm ID, OV-17 on 100/120 Gas Chrom Q, 170° to 230° C. at 20° C./minute) and each show 496 (M+).

What is claimed is:
1. The process for the preparation of a compound of the formula

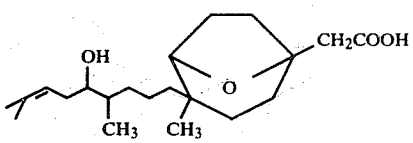

which comprises reacting a compound of the formula

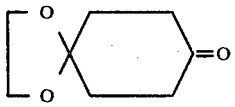

with diazoethane to form a cycloheptanone of the formula

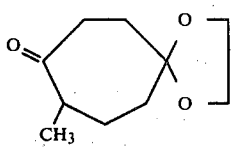

reacting the cycloheptanone with acrylonitrile to form a compound of the formula

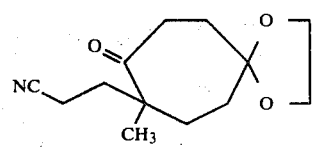

reacting the substituted cycloheptanone with a reducing agent to form a cycloheptanol of the formula

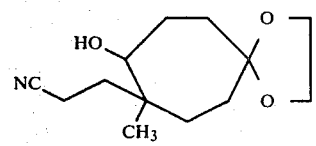

reacting the cycloheptanol with t-butyldiphenylsilyl chloride to form a compound of the formula

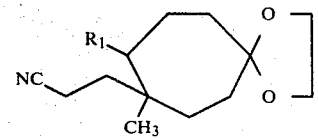

reacting the reaction product with an organic acid to form a ketone of the formula

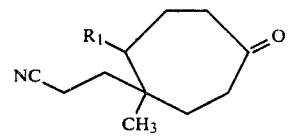

reacting the ketone with tetra-n-butylammonium fluoride to form a bicyclic hemiacetal of the formula

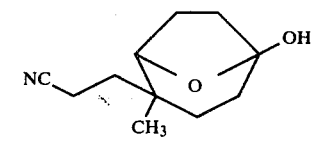

reacting the hemiacetal with trimethylorthoformate in the presence of a mineral acid to form an acetal of the formula

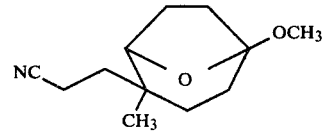

reacting the nitrile with diisobutylaluminum hydride to form an aldehyde of the formula

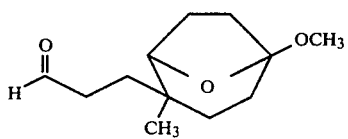

reacting the aldehyde with a compound of the formula

to form an unsaturated ester of the formula

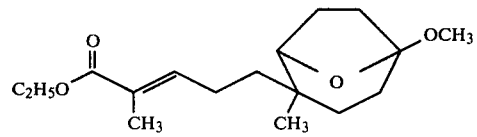

hydrogenating the unsaturated ester to form a saturated ester of the formula

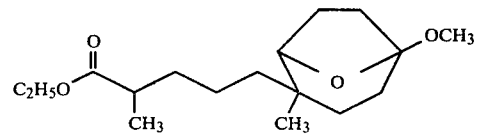

reducing the ester with diisobutylaluminum hydride to form an aldehyde of the formula

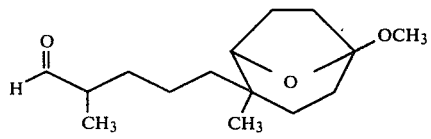

reacting the aldehyde with a Grignard reagent of the formula

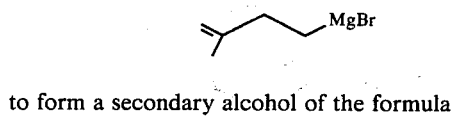

to form a secondary alcohol of the formula

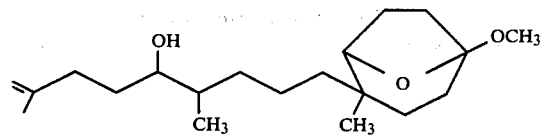

esterifying the alcohol with an esterifying agent to form an ester of the formula

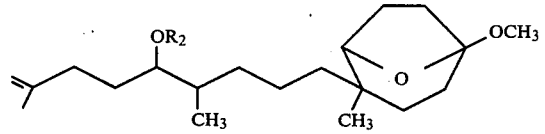

treating the ester with an acid selected from tosic acid and camphorsulfonic acid to form an ester of the formula

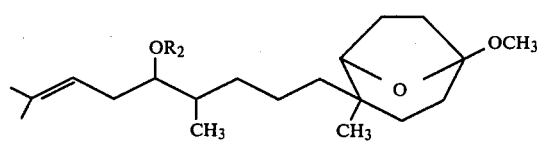

reacting the reaction product with acid to form a hemiacetal of the formula

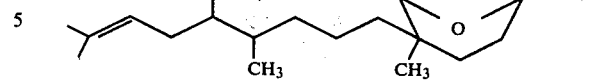

reacting the hemiacetal with a compound of the formula $(C_6H_5)_3P=CHCOOC_2H_5$ to form a diester of the formula

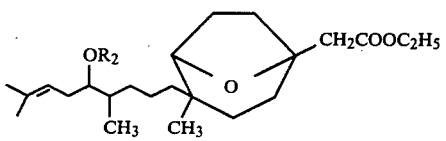

and hydrolyzing the ester with base, wherein $R_1$ is a t-butyldiphenylsilyoxy group and $R_2$ is benzoyl or a lower alkanoyl group having 2-5 carbon atoms.

2. The process of claim 1 wherein the reducing agent is sodium borohydride.

3. The process of claim 1 wherein the organic acid is acetic acid.

4. The process of claim 1 wherein the mineral acid is sulfuric acid.

5. The process of claim 1 wherein the esterifying agent is acetic anhydride.

6. The process of claim 1 wherein the acid is hydrochloric acid.

7. The process of claim 1 wherein the base is sodium hydroxide.

* * * * *